United States Patent
Yokouchi et al.

(10) Patent No.: US 9,826,893 B2
(45) Date of Patent: Nov. 28, 2017

(54) ELECTRONIC ENDOSCOPE SYSTEM AND LIGHT SOURCE FOR ENDOSCOPE

(71) Applicant: HOYA CORPORATION, Tokyo (JP)

(72) Inventors: Fumika Yokouchi, Tokyo (JP); Chinari Tanaka, Saitama (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/295,048

(22) Filed: Oct. 17, 2016

(65) Prior Publication Data

US 2017/0027429 A1 Feb. 2, 2017

Related U.S. Application Data

(63) Continuation of application No. 15/155,172, filed on May 16, 2016, which is a continuation of application
(Continued)

(30) Foreign Application Priority Data

Aug. 17, 2012 (JP) .................................. 2012-180902

(51) Int. Cl.
*A61B 1/00* (2006.01)
*A61B 1/06* (2006.01)
(Continued)

(52) U.S. Cl.
CPC ........ *A61B 1/0646* (2013.01); *A61B 1/00009* (2013.01); *A61B 1/00045* (2013.01);
(Continued)

(58) Field of Classification Search
CPC ........ A61B 1/06; A61B 1/0638; A61B 1/0646
(Continued)

(56) References Cited

U.S. PATENT DOCUMENTS 7,892,169 B2  2/2011  Gono et al.
7,949,387 B2  5/2011  Khoobehi et al.
(Continued)

FOREIGN PATENT DOCUMENTS

CN  103070658 A  5/2013
CN  103654687 A  3/2014
(Continued)

OTHER PUBLICATIONS

US 9,560,957, 02/2017, Yokouchi et al. (withdrawn)
(Continued)

*Primary Examiner* — Jeffery Williams
(74) *Attorney, Agent, or Firm* — Greenblum & Bernstein, P.L.C.

(57) ABSTRACT

A light source device for an electronic endoscope includes a light source that emits light having a visible light wavelength region and an optical filter that has transmission peaks at a plurality of particular wavelengths in a continuous wavelength region including the visible light wavelength region. The plurality of particular wavelengths include wavelengths of around 420 nm, around 550 nm and around 650 nm. The optical filter has a constant transmissivity higher than zero and lower than a half of each of the transmission peaks in a wavelength region between the transmission peaks and the constant transmissivity in the wavelength region between the transmission peaks is higher than a transmissivity in a wavelength region other than between the transmission peaks.

4 Claims, 5 Drawing Sheets

Related U.S. Application Data

No. 13/968,500, filed on Aug. 16, 2013, now Pat. No. 9,370,297.

(51) Int. Cl.
  *A61B 1/04* (2006.01)
  *A61B 1/07* (2006.01)

(52) U.S. Cl.
  CPC ............. *A61B 1/04* (2013.01); *A61B 1/06* (2013.01); *A61B 1/0638* (2013.01); *A61B 1/0661* (2013.01); *A61B 1/07* (2013.01)

(58) Field of Classification Search
  USPC .......................................................... 348/68
  See application file for complete search history.

(56) References Cited

U.S. PATENT DOCUMENTS

| | | | |
|---|---|---|---|
| 8,681,208 | B2 | 3/2014 | Yoshino |
| 8,913,111 | B2 | 12/2014 | Takahashi |
| 9,277,190 | B2 | 3/2016 | Igarashi et al. |
| 9,370,297 | B2 | 6/2016 | Yokouchi et al. |
| 9,414,741 | B2 | 8/2016 | Yamamoto |
| 9,591,966 | B2 | 3/2017 | Yokouchi et al. |
| 2003/0158470 | A1 | 8/2003 | Wolters et al. |
| 2003/0176768 | A1* | 9/2003 | Gono ............... A61B 1/0638 600/109 |
| 2005/0027166 | A1* | 2/2005 | Matsumoto ........... A61B 1/041 600/162 |
| 2010/0168584 | A1 | 7/2010 | Fujinuma et al. |
| 2011/0237915 | A1 | 9/2011 | Yamaguchi |
| 2011/0254937 | A1 | 10/2011 | Yoshino |
| 2012/0116159 | A1 | 5/2012 | Mizuyoshi et al. |
| 2012/0116192 | A1 | 5/2012 | Saito |
| 2012/0215066 | A1* | 8/2012 | Akiyama ........... A61B 1/00009 600/109 |
| 2012/0327205 | A1 | 12/2012 | Takahashi |
| 2013/0162790 | A1 | 6/2013 | Tanaka et al. |
| 2013/0289373 | A1 | 10/2013 | Yamamoto |
| 2013/0310668 | A1 | 11/2013 | Young |
| 2014/0152790 | A1 | 6/2014 | Saito et al. |
| 2014/0185907 | A1 | 7/2014 | Chiba |
| 2016/0058274 | A1 | 3/2016 | Chiba |
| 2016/0120449 | A1 | 5/2016 | Chiba |
| 2016/0146723 | A1 | 5/2016 | Chiba |

FOREIGN PATENT DOCUMENTS

| | | |
|---|---|---|
| CN | 103654690 A | 3/2014 |
| CN | 103796566 A | 5/2014 |
| CN | 105324064 A | 2/2016 |
| EP | 2449950 | 5/2012 |
| EP | 2468187 | 6/2012 |
| EP | 2689712 | 1/2014 |
| EP | 2702938 | 3/2014 |
| EP | 3005933 | 4/2016 |
| JP | H06-79594 B2 | 10/1994 |
| JP | 2002-95635 | 4/2002 |
| JP | 3559755 | 9/2004 |
| JP | 3583731 | 11/2004 |
| JP | 3607857 | 1/2005 |
| JP | 2007-29453 | 2/2007 |
| JP | 2011-10998 | 1/2011 |
| JP | 2011-224038 | 11/2011 |
| JP | 2012-100800 A | 5/2012 |
| JP | 2012-235962 A | 12/2012 |
| JP | 2012-245223 | 12/2012 |
| JP | 2013-39215 | 2/2013 |
| JP | 2013-63097 | 4/2013 |
| JP | 5362149 B1 | 12/2013 |
| JP | 2014-230647 | 12/2014 |
| JP | 2014-233344 | 12/2014 |
| WO | 2011/080996 | 7/2011 |
| WO | 2011/099322 | 8/2011 |
| WO | 2011/162111 | 12/2011 |
| WO | 2012/047806 | 4/2012 |
| WO | 2012/090552 A1 | 7/2012 |
| WO | 2013/047054 | 4/2013 |
| WO | 2014/192781 | 12/2014 |

OTHER PUBLICATIONS

Office Action issued in China Counterpart Patent Appl. No. 201310358808.2, dated Jan. 16, 2017, along with an english translation thereof.
Office Action issued in Japan Counterpart Patent Appl. No. 2012-180902, dated Dec. 26, 2016, along with an English translation thereof.
Office Action issued in Japan Counterpart Patent Appl. No. 2012-180902, dated May 24, 2016, along with an English translation thereof.
Office Action issued in China Counterpart Patent Appl. No. 201310358808.2, dated Jun. 24, 2016, along with an English translation thereof.
Office Action issued in China Counterpart Patent Appl. No. 201310358808.2, dated Nov. 4, 2015, along with an English translation thereof.
Office Action issued in European Counterpart Patent Appl. No. 14805121.2, dated Mar. 20, 2017.
Extended European Search Report issued in European Patent Appl. No. 16175262.1, dated Nov. 17, 2016.
Office Action issued in European Counterpart Patent Appl. No. 15183306.8, dated Jan. 24, 2017.
European Search Report issued in European Patent Application No. 15195635.6, dated Apr. 18, 2016.
European Search Report issued in European Patent Application No. 15183306.8, dated Feb. 5, 2016.
U.S. Appl. No. 14/936,965 to Toru Chiba, filed Nov. 10, 2015.
U.S. Appl. No. 14/837,300 to Toru Chiba, filed Aug. 27, 2015.
U.S. Appl. No. 14/894,119 to Toru Chiba, filed Nov. 25, 2015.
U.S. Appl. No. 15/295,048 to Fumika Yokouchi et al., filed Oct. 17, 2016.
International Search Reporting (ISR) in International Application PCT/JP2016/058112, dated Jun. 7, 2016.
Office Action issued in Japan Patent Appl. No. 2014-179036, dated Feb. 23, 2017.
Office Action issued in China Patent Appl. No. 201510549104.2, dated Apr. 18, 2017, along with an English-language translation thereof.
U.S. Appl. No. 15/308,479 to Fumika Yokouchi, which was filed on Nov. 2, 2016.

* cited by examiner

ELECTRONIC ENDOSCOPE SYSTEM AND LIGHT SOURCE FOR ENDOSCOPE

CROSS-REFERENCED RELATED APPLICATIONS

The present application is a continuation of U.S. applicaton Ser. No. 15/155,172 filed on May 16, 2016, which is a continuation of U.S. application Ser. No. 13/968,500 filed on Aug. 16, 2013, the disclosure of which is incorporated herein by reference in its entirety.

BACKGROUND OF THE INVENTION

The present invention relates to an electronic endoscope system and a light source for an endoscope for observing a color image of an object, and particularly to an electronic endoscope system and a light source for an endoscope suitably configured to allow an operator to observe a particular biological structure.

As a system for making a diagnosis on a body cavity of a patient, an electronic endoscope system is known and in practical use. Among such electronic endoscope systems, there is an electronic endoscope system configured to illuminate an object through a narrow band filter letting light with a certain wavelength band for which a particular biological structure shows a high degree of absorption pass therethrough, and to generate a spectral image highlighting the particular biological structure by receiving a scattered component of the light from the object, so that tissue information of the biological structure can be visualized.

In Japanese Patent Publication No. 3583731 (hereafter, referred to as patent document 1), an example of an endoscope apparatus for making an observation by narrow-band light is described. In the endoscope apparatus described in patent document 1, a narrow band filter configured to narrow a bandwidth of at least one of wavelength regions of illumination light is arranged on an optical path proceeding from an illumination light supply unit to an image pick-up unit and a band image of an object having a discrete spectral distribution obtained by the narrow-band light is generated. By using the endoscope apparatus of this type, it becomes possible to visually recognize tissue information of a particular biological structure of the object in a manner in which the tissue information is layered. As a result, tissue information at a desired depth in a tissue surface of the biological structure can be obtained.

SUMMARY OF THE INVENTION

However, in the endoscope apparatus described in patent document 1, information cannot be obtained in a wavelength band other than a transmitted main wavelength because the illumination light has the discrete spectral distribution. Therefore, there is a possibility that tissue information of the object is partially lost. Furthermore, since a transmission range of the illumination light is limited by the narrow band filter, the amount of light is decreased and thereby the brightness of the obtained image decreases.

The present invention is made in consideration of the above described circumstances. The present invention is advantageous in that it provides an electronic endoscope system and a light source for an endoscope configured, when a particular biological structure is observed with narrow-band light, to prevent loss of information concerning a particular biological structure and to enhance the brightness and contrast of an image.

According to an aspect of the invention, there is provided an electronic endoscope system, which includes: a light source that emits light having a visible light wavelength region; an optical filter that has transmission peaks at least at two particular wavelengths in a continuous wavelength region including the visible light wavelength region and has a transmissivity higher than zero and lower than a half of each transmission peak between the transmission peaks of the at least two particular wavelengths; a solid-state image pick-up device that receives reflected light from an object which is irradiated with illumination light via the optical filter; and an image generation unit configured to generate a color image to be displayed on a monitor by processing an image signal outputted by the solid-state image pick-up device. The optical filter has a transmissivity of zero at a wavelength region other than an interval between the transmission peaks of the at least two particular wavelengths.

When an object is illuminated via the above described optical filter, a spectral image of which brightness and contrast are enhanced can be generated and displayed on a monitor. Furthermore, since information on a wavelength region between the transmission peaks of the particular wavelengths can be obtained, occurrence of lack of information can be prevented. That is, it becomes possible to enhance brightness and contrast while preventing of occurrence of lack of information when a particular biological structure is observed through use of narrow band light.

The at least two particular wavelengths may include a wavelength region of around 420 nm at which hemoglobin has a larger absorptive property. With this configuration, it becomes possible to observe vessel structures near a surface layer and in a deep layer.

The electronic endoscope system may further include: an optical filter switching unit configured to cause the optical filter to be inserted into or retracted from an illumination optical path of the light source; and an operation unit configured to receive a user operation. The optical filter switching unit may cause the optical filter to be inserted into or retracted from the illumination optical path in accordance with the user operation received through the operation unit. By thus retracting the optical filter from the illumination optical path as the need arises, it becomes possible to display a normal color image on the monitor.

According to another aspect of the invention, there is provided a light source for an endoscope, which includes: a light source that emits light having a visible light wavelength region; and an optical filter that has transmission peaks at least at two particular wavelengths in a continuous wavelength region including the visible light wavelength region and has a transmissivity higher than zero and lower than a half of each transmission peak between the transmission peaks of the at least two particular wavelengths. The optical filter has a transmissivity of zero at a wavelength region other than an interval between the transmission peaks of the at least two particular wavelengths.

With this configuration, it becomes possible to enhance brightness and contrast while preventing of occurrence of lack of information when a particular biological structure is observed through use of narrow band light.

BRIEF DESCRIPTION OF THE ACCOMPANYING DRAWINGS

DETAILED DESCRIPTION OF THE EMBODIMENTS

Hereinafter, an embodiment according to the invention is described with reference to the accompanying drawings.

Figure 1:
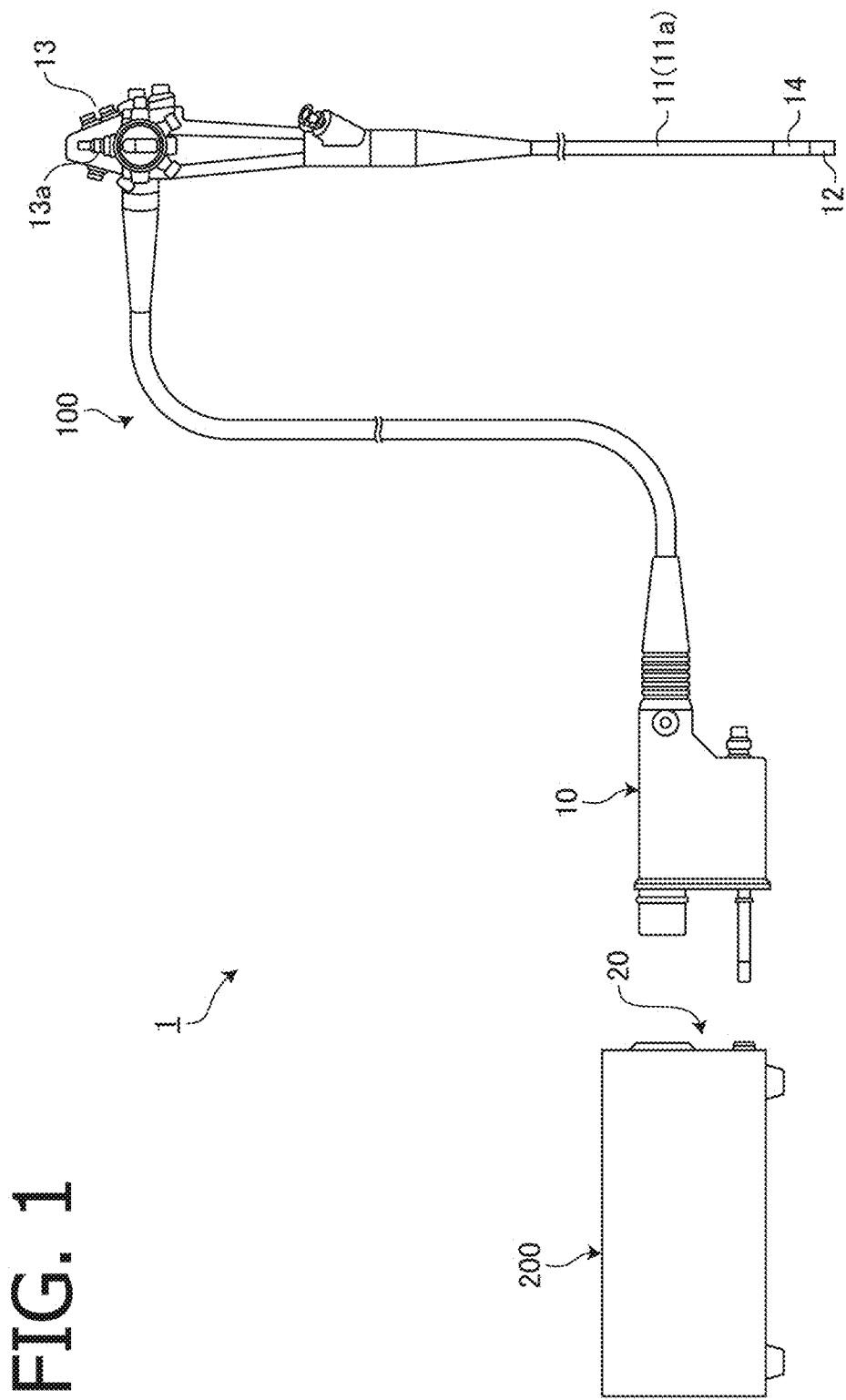
FIG. 1 is illustrates an outer appearance of an electronic endoscope system according to an embodiment of the invention.

FIG. 1 illustrates an outer appearance of an electronic endoscope system 1 according to the embodiment. As shown in FIG. 1, the electronic endoscope system 1 has an electronic scope 100 for imaging an object. The electronic scope 100 includes a flexible tube 11 covered with a sheath 11 a having flexibility. To a tip of the flexible tube 11, a tip part unit 12 externally covered with a resin housing having rigidity is coupled. A bending part 14 arranged between the flexible tube 11 and the tip part unit 12 is configured to freely bend through remote control from a forehand operation unit 13 (e.g., a rotating operation to a bending operation knob 13a) attached to a proximal end of the flexible tube 11. This bending mechanism has a known configuration installed in a general electronic scope, and is configured to bend the bending part 14 by drawing an operation wire provided in the flexible tube 11 in conjunction with a rotational operation to the bending operation knob 13a. By changing the direction of the tip part unit 12 through the above described bending operation, an imaging area of the electronic scope 100 can be moved.

As shown in FIG. 1, the electronic endoscope system 1 has a processor 200. The processor 200 is integrally provided with a signal processing device which processes signals from the electronic scope 100, and a light source which illuminates, through the electronic scope 100, a body cavity to which natural light does not reach. In another embodiment, the signal processing device and the light source may be provided as separate devices.

The processor 200 is provided with a connector part 20 corresponding to a connector part 10 provided at the proximal end of the electronic scope 100. The connector part 20 has a structure corresponding to a structure of the connector part 10, and is configured to connect the processor 200 with the electronic scope 100 electrically and optically.

Figure 2:
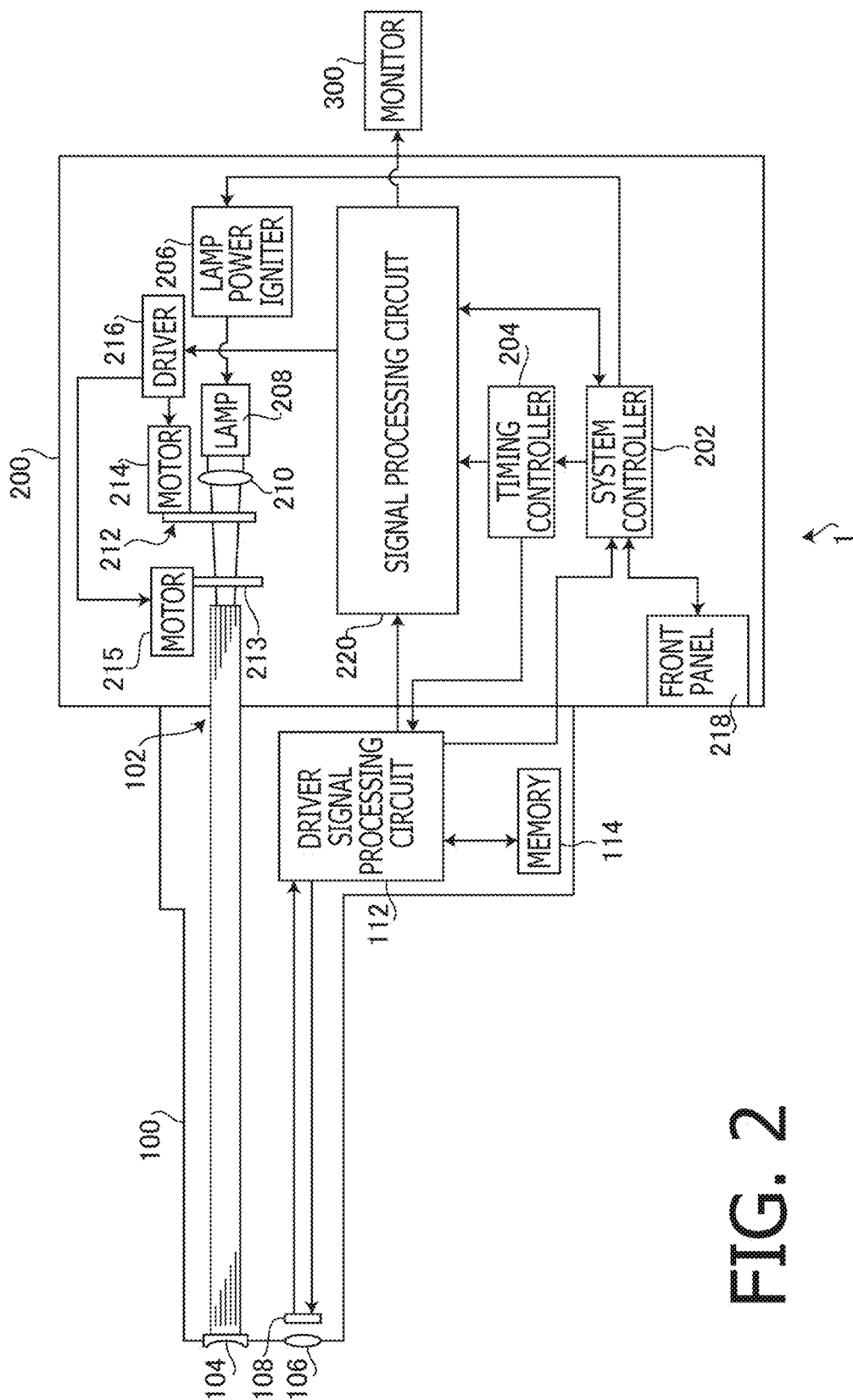
FIG. 2 is a block diagram illustrating a configuration of the electronic endoscope system according to the embodiment.

FIG. 2 is a block diagram illustrating a configuration of the electronic endoscope system 1. As shown in FIG. 2, the electronic endoscope system 1 has a monitor 300 connected to the processor 200 via a cable. It should be noted that in FIG. 1 the monitor 300 is omitted for the sake of simplicity.

As shown in FIG. 2, the processor 200 has a system controller 202 and a timing controller 204. The system controller 202 controls various components constituting the electronic endoscope system 1. The timing controller 204 outputs clock pulses for adjusting signal processing timings to various circuits in the electronic endoscope system 1.

After activation by a lamp power igniter 206, a lamp 208 emits light having a spectral property expanding from a visible light region to an infrared region, i.e., an invisible light region (or light including at least a visible light region).

As the lamp 208, a high luminance lamp, such as a xenon lamp, a halogen lamp or a metal halide lamp, is suitable. The illumination light emitted from the lamp 208 is condensed by a condensing lens 210 and is limited via an aperture stop 212 to have a suitable light amount.

To the aperture stop 212, a motor 214 is mechanically coupled via a transmission mechanism, such as an arm and a gear, not shown. The motor 214 is, for example, a DC motor, and is driven under control of a driver 216. The aperture stop 212 is activated by the motor 214 to change the aperture size thereof. In order to adjust the brightness of an image displayed on the monitor 300 to have a suitable brightness, the aperture stop 212 limits the light amount of the light emitted from the lamp 208 depending on the aperture size thereof. A reference value regarding a suitable brightness of an image can be set or changed in response to an adjusting operation for luminance by an operator through a front panel 218. Since a photochromatic circuit which adjusts luminance by controlling the driver 216 is a known circuit, explanation thereof is omitted.

Various types of forms can be considered as the configuration of the front panel 218. Examples of a specific configuration of the front panel 218 include hardware keys provided for the respective functions mounted on a front surface of the processor 200, a touch panel GUI (Graphical User Interface) and a combination of hardware keys and a GUI.

The illumination light which has passed through the aperture stop 212 is spectrally divided by an optical filter 213, and is incident on an entrance end face of a LCB (Light Carrying Bundle) 102. To the optical filter 213, a motor 215 driven under control of the driver 216 is mechanically coupled via a transmission mechanism, such as an arm and a gear, not shown. The motor 215 drives the optical filter 213 so that the optical filter 213 is inserted into or retracted from an optical path in response to a switching operation to the front panel 218 by the operator. While the optical filter 213 is at a retracted position from the optical path, the illumination light which passed the aperture stop 212 directly enters the entrance end face of the LCB 102. As the motor 215, a galvano motor or a servo motor can be considered.

The illumination light which has entered the entrance end face of the LCB 102 propagates through the LCB 102 while repeating total reflection. The illumination light which has propagated the LCB 102 emerges from an exit end face of the LCB 102 arranged at the tip of the electronic scope 100. The illumination light emerging from the exit end face of the LCB 102 illuminates the object via a light distribution lens 104. The reflected light from the object is converged by an objective lens 106 to form an optical image on pixels of a light-receiving surface of a solid-state image pick-up device 108.

The solid-state image pick-up device 108 is, for example, a single-chip color CCD (Charge Coupled Device) imaging sensor, and is configured to accumulate charges responsive to the light amount of the optical image formed on the pixels of the light-receiving surface and to convert the charges into an image signal corresponding to R, G and B. After being amplified by a pre-amplifier not shown, the converted image signal is outputted to a signal processing circuit 220 via a driver signal processing circuit 112. In another embodiment, the solid-state image pick-up device 108 may be a CMOS (Complementary Metal Oxide Semiconductor) imaging sensor.

The driver signal processing circuit 112 accesses a memory 114 to read out unique information of the electronic scope 100. The unique information of the electronic scope 100 includes, for example, the number of pixels, sensitivity, a supported rate and a model number of the solid-state image pick-up device 108. The driver signal processing circuit 112 outputs the unique information read from the memory 114, to the system controller 202.

Based on the unique information of the electronic scope 100, the system controller 202 executes various calculations and generates control signals. Using the generated control signals, the system controller 202 controls the operation and timing of various circuits in the processor 200 so that processes suitable for an electronic scope being connected to the processor 200 can be achieved. The system controller 202 may have a table in which a model number and control information suitable for the electronic scope of the model number are associated. In such a case, the system controller 202 refers to the control information in the table, and controls the operation and timing of the various circuits in the processor 200 so that processes suitable for an electronic scope being connected to the processor 200 can be performed.

In accordance with the timing control by the system controller 202, the timing controller 204 supplies clock pulses to the driver signal processing circuit 112. In accordance with the clock pulses supplied from the timing controller 204, the driver signal processing circuit 112 drives and controls the solid-state image pick-up device 108 at timing synchronizing with a frame rate of images processed by the processor 200 side.

To the signal processing circuit 220, the image signal is inputted from the driver signal processing circuit 112. The image signal is subjected to various processes including a clamping process, a knee process, γ-process, an interpolation process, AGC (Auto Gain Control) and A-D conversion, and thereafter is buffered into frame memories respectively corresponding to R, G and B, at a frame rate. Each buffered color signal is swept out at timing controlled by the timing controller 204, and is converted into a video signal based on a predetermined standard, such as an NTSC (National Television System Committee) or a PAL (Phase Alternating Line). By sequentially inputting the converted video signal into the monitor 300, an image of the object is displayed on the monitor 300. While the object is illuminated by inserting the optical filter 213 into the optical path, a spectral image highlighting a particular biological tissue (e.g., blood vessels are separated in a layer structure (a blood vessel in a surface layer and a blood vessel in a deep layer are displayed in different colors)) is generated and displayed. While the object is illuminated in a state where the optical filter 213 is retracted from the optical path, a normal color image is generated and displayed. When a spectral image is generated, a color conversion process which is different from that for a normal color image is performed.

Figure 3:
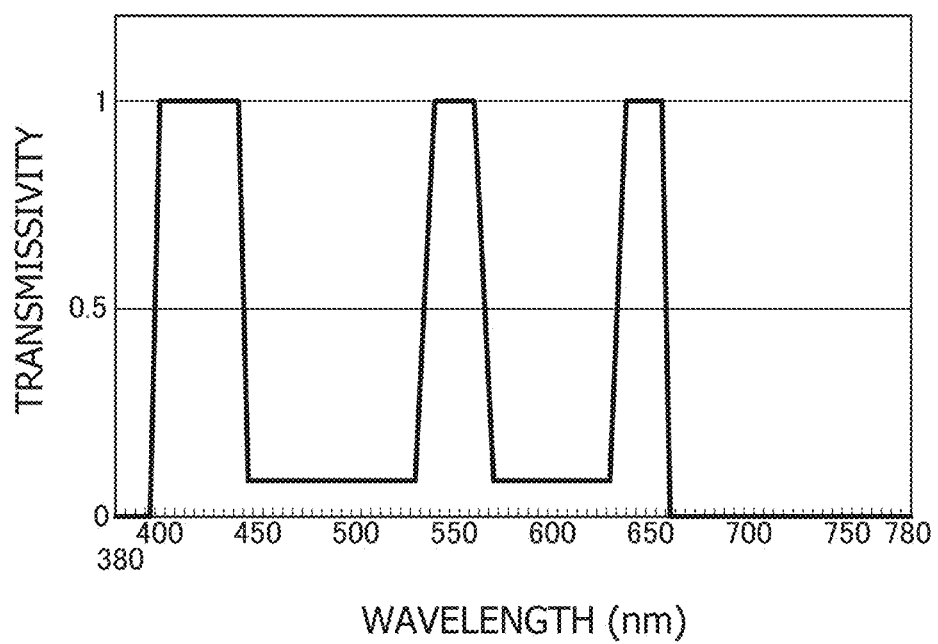
FIG. 3 is a graph illustrating a spectral property of an optical filter provided in a processor according to the embodiment.

FIG. 3 is a graph illustrating a spectral property of the optical filter 213. In FIG. 3, the vertical axis represents a normalized transmissivity, and a horizontal axis represents a wavelength (unit: nm). As shown in FIG. 3, the spectral property of the optical filter 213 has transmission peaks around 420 nm, 550 nm and 650 nm, respectively, and has a transmissivity higher than or equal to a certain value between the transmission peaks.

The transmissivity defined between the transmission peaks is higher than zero and lower than a half of the each transmission peaks. In this embodiment, by intentionally setting the transmissivity for light other than the particular wavelength for highlighting the particular biological tissue to be higher than zero, the light amount cut by the optical filter 213 is suppressed and the brightness of the spectral image is enhanced. Furthermore, since information regarding regions between the transmission peaks can also be obtained, occurrence of lack of information can be prevented. Furthermore, by setting the transmissivity to be lower than a half of each transmission peak, deterioration of detection sensitivity with respect to the particular biological tissue can be suppressed effectively. It is more preferable that the lower limit of the tranmsissivity between the transmission peaks is higher than or equal to 5% of each transmission peak, and the upper limit of the transmissivity between the transmission peaks is lower than or equal to 10% of each transmission peak. By thus setting the transmissivity, it becomes possible to obtain an image having a high degree of contrast while maintaining a certain degree of brightness.

Furthermore, in the optical filter 213 according to the embodiment, transmissivity of a wavelength region other than the intervals between the transmission peaks is zero. As a result, it becomes possible to eliminate an undesirable red component in comparison with the case where the transmissivity higher than the certain value is maintained over the entire region from the visible light region to the infrared light region (e.g., 380 nm to 1000 nm). Consequently, an image having a higher degree of contrast can be obtained. That is, according to the embodiment, it is possible to generate a spectral image having a higher degree of brightness and contrast, and display such an image on the monitor 300, by illuminating an object via the optical filter 213. It is also possible to prevent occurrence of lack of information.

Figure 4A:
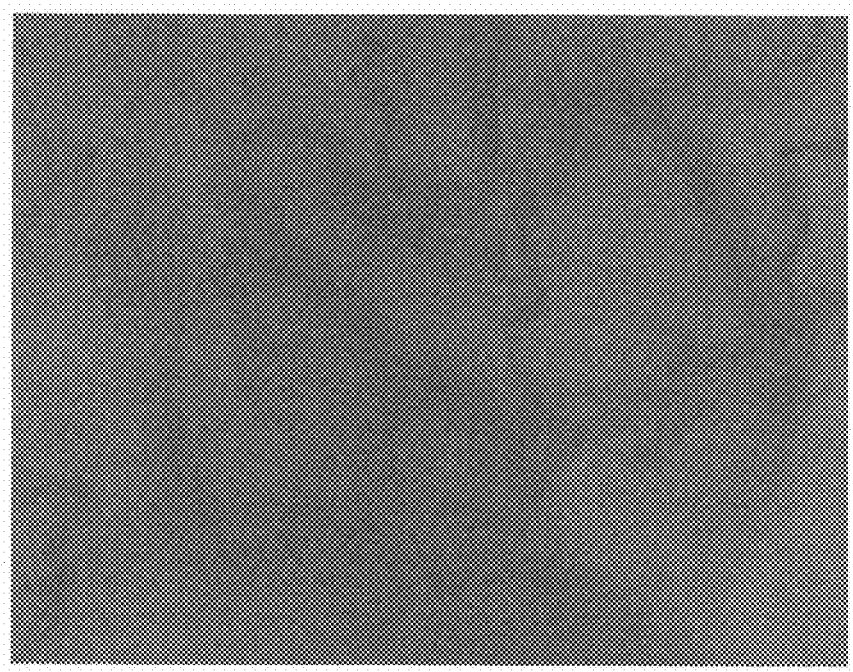
FIG. 4A illustrates an observation image obtained when an object is illuminated without using the optical filer.
Figure 4B:
FIG. 4B illustrates an observation image obtained when the object is illuminated via the optical filter.

FIG. 4A illustrates an observation image obtained when an object is illuminated without using the optical filer 213. FIG. 4B illustrates an observation image obtained when the object is illuminated via the optical filter 213. The images in FIGS. 4A and 4B are obtained by shooting the same object (a buccal cavity). As shown in FIG. 4A, when the optical filter 213 is not used, a mucous membrane structure in a buccal cavity is observed as a brighter image. Since the particular biological structure is not highlighted, the image is totally represented as a smooth expressionless image in FIG. 4A. On the other hand, when the optical filter 213 is used, the particular biological structure is highlighted, and the mucous membrane structure in the buccal cavity can be observed in a single image together with the particular biological structure as shown in FIG. 4B. The wavelength band around 420 nm or 550 nm corresponding to the transmission peak is an absorption band for hemoglobin. Specifically, the wavelength around 420 nm is more absorptive to hemoglobin than the wavelength around 550 nm. Therefore, the particular biological structure observed in this case is blood vessels in the buccal cavity. Even when the illumination light is provided via the optical filter 213, the illumination light is not narrow band light but has a certain degree of broadness. Such a configuration makes it possible to prevent occurrence of lack of information, and to observe various types of biological structures corresponding to respective invasion depths of wavelengths. As a result, diagnostic performance can be enhanced.

Figure 5:
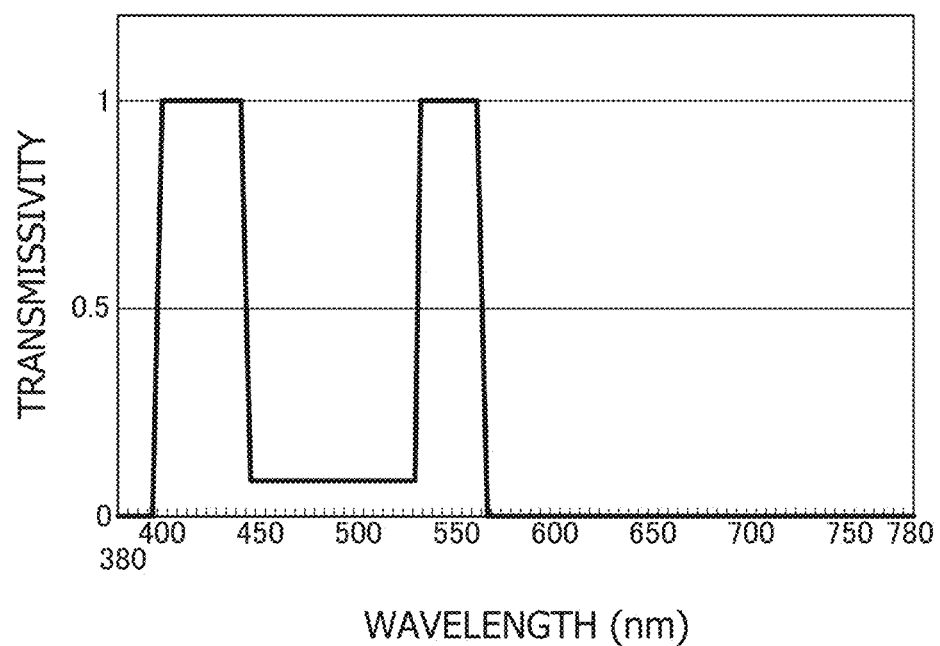
FIG. 5 shows a spectral property of an optical filter provided in a processor according to another embodiment.

The foregoing is explanation about the embodiment. It is noted that the present invention is not limited to the above described configuration, and can be varied within the scope of the invention. For example, the spectral property of the optical filter 213 is not limited to that show in FIG. 3, and may be set depending on the type of a biological structure to be observed. As another example of a spectral property, FIG. 5 shows a spectral property of an optical filter 213'. In FIG. 5, the vertical axis represents a normalized transmissivity, and the horizontal axis represents the wavelength (unit: nm).

As shown in FIG. 5, the spectral property of the optical filter 213' has transmission peaks around 420 nm and 550 nm, and has a transmissivity higher than or equal to a certain value between the transmission peaks. As in the case of FIG. 3, the transmissivity higher than or equal to the certain value between the transmission peaks is higher than or equal to zero and is lower than a half of the transmission peaks, and is preferably 5% to 10% of the transmission peak. In contrast to the optical filter 213 shown in FIG. 3 having the transmission peaks at the three wavelength bands so that a natural color image is obtained, the optical filter 213' shown in FIG. 5 has transmission peaks at two wavelength bands so as to be able to obtain an image having a high contrast.

This application claims priority of Japanese Patent Application No. P2012-180902, filed on Aug. 17, 2012. The entire subject matter of the application is incorporated herein by reference.

What is claimed is:

1. An electronic endoscope system, comprising:
a light source that emits light having a visible light wavelength region;
an optical filter that has transmission peaks at a plurality of particular wavelengths in a continuous wavelength region including the visible light wavelength region;
a solid-state image pick-up device that receives reflected light from an object which is irradiated with illumination light via the optical filter; and
an image generator configured to generate a color image to be displayed on a monitor by processing an image signal output by the solid-state image pick-up device,
wherein the plurality of particular wavelengths include wavelengths of around 420 nm, and around 550 nm and/or around 650 nm,
wherein a band width of a transmission peak wavelength of around 420 nm of the plurality of particular wavelengths is larger than band widths of other transmission peak wavelengths of the plurality of particular wavelengths,
wherein the optical filter is configured such that:
the optical filter has a transmissivity higher than zero and equal to or lower than 10% of each of the transmission peaks in a wavelength region between the transmission peaks; and
the transmissivity in the wavelength region between the transmission peaks is higher than a transmissivity in a wavelength region other than between the transmission peaks.

2. The electronic endoscope system according to claim 1, wherein the transmissivity between the transmission peaks is within a range of 5% to 10% of each of the transmission peaks.

3. The electronic endoscope system according to claim 1, further comprising:
an optical filter switcher configured to cause the optical filter to be inserted into or retracted from an illumination optical path of the light source; and
an operator configured to receive a user operation,
wherein the optical filter switcher causes the optical filter to be inserted into or retracted from the illumination optical path in accordance with the user operation received through the operator.

4. A light source device for an electronic endoscope, comprising:
a light source that emits light having a visible light wavelength region; and
an optical filter that has transmission peaks at a plurality of particular wavelengths in a continuous wavelength region including the visible light wavelength region;
wherein the plurality of particular wavelengths include wavelengths of around 420 nm, and around 550 nm and/or around 650 nm,
wherein a band width of a transmission peak wavelength of around 420 nm of the plurality of particular wavelengths is larger than band widths of other transmission peak wavelengths of the plurality of particular wavelengths,
wherein the optical filter is configured such that:
the optical filter has a transmissivity higher than zero and lower than a half of each of the transmission peaks in a wavelength region between the transmission peaks; and
the transmissivity in the wavelength region between the transmission peaks is higher than a transmissivity in a wavelength region other than between the transmission peaks.

* * * * *